(12) United States Patent
Moskowitz et al.

(10) Patent No.: US 12,122,864 B2
(45) Date of Patent: Oct. 22, 2024

(54) POLYMER FOR THE PRODUCTION OF CARBON FIBERS AND CARBON FIBERS MADE THEREFROM

(71) Applicant: Cytec Industries Inc., Princeton, NJ (US)

(72) Inventors: Jeremy Moskowitz, Mauldin, SC (US); William Jacobs, Bethel, CT (US); Amy Tucker, Central, SC (US); Billy Harmon, Simpsonville, SC (US)

(73) Assignee: Cytec Industries Inc., Princeton, NJ (US)

( * ) Notice: Subject to any disclaimer, the term of this patent is extended or adjusted under 35 U.S.C. 154(b) by 686 days.

(21) Appl. No.: 17/255,643

(22) PCT Filed: Jul. 2, 2019

(86) PCT No.: PCT/US2019/040277
§ 371 (c)(1),
(2) Date: Dec. 23, 2020

(87) PCT Pub. No.: WO2020/010069
PCT Pub. Date: Jan. 9, 2020

(65) Prior Publication Data
US 2021/0284774 A1    Sep. 16, 2021

Related U.S. Application Data

(60) Provisional application No. 62/693,114, filed on Jul. 2, 2018.

(51) Int. Cl.
| | | |
|---|---|---|
| *C08F 220/00* | (2006.01) | |
| *C07C 277/08* | (2006.01) | |
| *C08F 220/18* | (2006.01) | |
| *C08F 220/44* | (2006.01) | |
| *C08F 220/46* | (2006.01) | |
| *C08F 220/48* | (2006.01) | |
| *D01D 1/02* | (2006.01) | |
| *D01D 1/04* | (2006.01) | |
| *D01D 1/06* | (2006.01) | |
| *D01D 10/06* | (2006.01) | |
| *D01F 6/38* | (2006.01) | |
| *D01F 9/21* | (2006.01) | |
| *D01F 9/22* | (2006.01) | |

(52) U.S. Cl.
CPC .......... *C08F 220/44* (2013.01); *C07C 277/08* (2013.01); *C08F 220/1805* (2020.02); *C08F 220/46* (2013.01); *D01D 1/02* (2013.01); *D01D 1/04* (2013.01); *D01D 10/06* (2013.01); *D01F 6/38* (2013.01); *D01F 9/22* (2013.01)

(58) Field of Classification Search
CPC .... C08F 220/00; C08F 220/44; C08F 220/46; C08F 220/48; D01F 9/21; D01F 9/22; D01D 1/02; D01D 1/04; D01D 1/06
See application file for complete search history.

(56) References Cited

U.S. PATENT DOCUMENTS

| 5,650,465 A | 7/1997 | Ryan et al. |
| 2016/0355686 A1 | 12/2016 | Dikan et al. |

FOREIGN PATENT DOCUMENTS

| WO | 9500560 A1 | 1/1995 |
| WO | 2011101460 A2 | 8/2011 |

OTHER PUBLICATIONS

Menyashev, M.R. et al., "Guanidine Methacrylate and Methacryloyl Guanidine Hydrochloride: Synthesis and Polymerization", Polymer Science, Series B., 2016, vol. 58, No. 5, pp. 556-563 (see p. 557).

*Primary Examiner* — Caixia Lu
(74) *Attorney, Agent, or Firm* — Osha Bergman Watanabe & Burton LLP

(57) ABSTRACT

A polymer comprising repeating units derived from a first monomer, typically acrylonitrile, and repeating units derived from a second monomer different from the first monomer, wherein the second monomer is a compound comprising an ethylenically unsaturated organic anion and an organic cation containing a C=N imine group; a process for producing carbon fibers using the said polymer; and carbon fibers made therefrom, are described herein.

17 Claims, 2 Drawing Sheets

POLYMER FOR THE PRODUCTION OF CARBON FIBERS AND CARBON FIBERS MADE THEREFROM

CROSS REFERENCE TO RELATED APPLICATIONS

The present application is a U.S. national phase entry under 35 U.S.C. § 371 of International Application No. PCT/US2019/040277, filed on Jul. 2, 2019, which claims priority of U.S. Provisional Application No. 62/693,114, filed Jul. 2, 2018. The entire contents of these applications are explicitly incorporated herein by this reference.

FIELD OF THE INVENTION

The present disclosure relates generally to a polymer comprising repeating units derived from a first monomer, typically acrylonitrile, and repeating units derived from a second monomer different from the first monomer, wherein the second monomer is a compound comprising an ethylenically unsaturated organic anion and an organic cation containing a C=N imine group. The present disclosure also relates to a process for producing carbon fibers using the said polymer, and carbon fibers made therefrom.

BACKGROUND

Carbon fibers have been used in a wide variety of applications because of their desirable properties, such as high strength and stiffness, high chemical resistance and low thermal expansion. For example, carbon fibers can be formed into a structural part that combines high strength and high stiffness, while having a weight that is significantly lighter than a metal component of equivalent properties. Increasingly, carbon fibers are being used as structural components in composite materials for aerospace and automotive applications, among others. In particular, composite materials have been developed wherein carbon fibers serve as a reinforcing material in a resin or ceramic matrix.

Carbon fiber from acrylonitrile is generally produced by a series of manufacturing steps or stages. Acrylonitrile monomer is first polymerized by mixing it with one or more comonomers (e.g., itaconic acid, methacrylic acid, methyl acrylate and/or methyl methacrylate) and reacting the mixture with a catalyst to form polyacrylonitrile (PAN) polymer. PAN is currently the most widely used precursor for carbon fibers.

Once polymerized, the PAN polymer may be isolated by typical means or provided as a solution (i.e., spin "dope"). PAN polymer may be converted into precursor fibers by any number of methods known to those of ordinary skill in the art, including, but not limited to, melt spinning, dry spinning, wet spinning, gel spinning, among others.

In one method (dry spinning), the heated dope is pumped (filtered) through tiny holes of a spinnerette into a tower or chamber of heated inert gas where the solvent evaporates, leaving a solid fiber.

In another method (wet spinning), the heated polymer solution ("spinning dope") is pumped through tiny holes of a spinnerette into a coagulation bath where the spinning dope coagulates and solidifies into fibers. Wet spinning can be further divided into one of the minor processes of (1) wet-jet spinning, wherein the spinnerette is submerged in the coagulation bath; (2) air gap or dry jet spinning, wherein the polymer jets exit the spinnerette and pass through a small air gap (typically 2-10 mm) prior to contacting the coagulation bath; and (3) gel spinning, wherein the dope is thermally induced to phase change from a fluid solution to a gel network. In both dry and wet spinning methods, the fiber is subsequently washed and stretched through a series of one or more baths.

After spinning and stretching the precursor fibers and before they are carbonized, the fibers need to be chemically altered to convert their linear molecular arrangement to a more thermally stable molecular ladder structure. This is accomplished by heating the fibers in air to about 200-300° C. (about 390-590° F.) for about 30-120 minutes. This causes the fibers to pick up oxygen molecules from the air and rearrange their atomic bonding pattern. This oxidation or thermal stabilization step can occur by a variety of processes, such as drawing the fibers through a series of heated chambers or passing the fibers over hot rollers.

After oxidation, the stabilized precursor fibers are heated (carbonized) to a maximum temperature of about 1000-3000° C. (about 1800-5500° F.) for several minutes in one or two furnaces filled with a gas mixture free of oxygen. As the fibers are heated, they begin to lose their non-carbon atoms in the form of various gases such as water vapor, hydrogen cyanide, ammonia, carbon monoxide, carbon dioxide, hydrogen and nitrogen. As the non-carbon atoms are expelled, the remaining carbon atoms form tightly bonded carbon crystals that are aligned parallel to the long axis of the fiber.

The resultant carbon fibers have a surface that does not bond well with epoxies and other materials used in composite materials. To give the fibers better bonding properties, their surface may be slightly oxidized. The addition of oxygen atoms to the surface provides better chemical bonding properties and also removes weakly bound crystallites for better mechanical bonding properties. Once oxidized, the carbon fibers may be coated ("sized") to protect them from damage during winding or weaving.

Oxidation of precursor fibers is a time consuming step in the continuous manufacturing of carbon fiber. The high oven temperatures and slow throughput inhibits efforts to reduce cost. Several means to address the issue of slow oxidation, including plasma treatment, microwave, proton irradiation, and chemical post-spinning treatments, are known. However, the production feasibility of such methods has not been realized and the means to control such methods in a continuous fashion is still underdeveloped.

Herein, a new strategy for the production of carbon fibers that employs a polymer comprising repeating units derived from a first monomer, typically acrylonitrile, and repeating units derived from a second monomer different from the first monomer, wherein the second monomer is a compound comprising an ethylenically unsaturated organic anion and an organic cation containing a C=N imine group, and that would address one or more of the aforementioned disadvantages is described.

SUMMARY OF THE INVENTION

It has been discovered that the use of a compound comprising an ethylenically unsaturated organic anion and an organic cation containing a C=N imine group as second monomer in the production of the polymer described herein allows for cost/energy savings as well as reduction or elimination of the use of ammonia on the resulting polymer, among other advantages.

Thus, in a first aspect, the present disclosure relates to a process for producing a compound comprising an ethylenically unsaturated organic anion and an organic cation containing a C=N imine group, the process comprising reacting an ethylenically unsaturated organic acid, or anhydride thereof, with an organic base containing a C=N imine group.

In a second aspect, the present disclosure relates to a polymer comprising repeating units derived from a first monomer, typically acrylonitrile, and repeating units derived from a second monomer different from the first monomer, wherein the second monomer is a compound comprising an ethylenically unsaturated organic anion and an organic cation containing a C=N imine group.

In a third aspect, the present disclosure relates to a process for producing a polymer described herein, the process comprising copolymerizing a first monomer, typically acrylonitrile, and a second monomer different from the first monomer, wherein the second monomer is a compound comprising an ethylenically unsaturated organic anion and an organic cation containing a C=N imine group.

In a fourth aspect, the present disclosure relates to a process for producing carbon fibers, the process comprising:
a) preparing a polymer solution or a molten polymer;
b) spinning the polymer solution or the molten polymer prepared in step (a); thereby forming carbon fiber precursor fibers;
c) drawing the carbon fiber precursor fibers through one or more draw and wash baths, resulting in drawn carbon fiber precursor fibers that are substantially free of solvent; and
d) oxidizing the drawn carbon fiber precursor fibers of step c) to form stabilized carbon fiber precursor fibers and then carbonizing the stabilized carbon fiber precursor fiber, thereby producing carbon fibers;
wherein the polymer solution or molten polymer comprises a polymer described herein or a polymer made according to the process described herein.

In a fifth aspect, the present disclosure relates to carbon fibers produced according to the process described herein.

DETAILED DESCRIPTION

Figure 1:
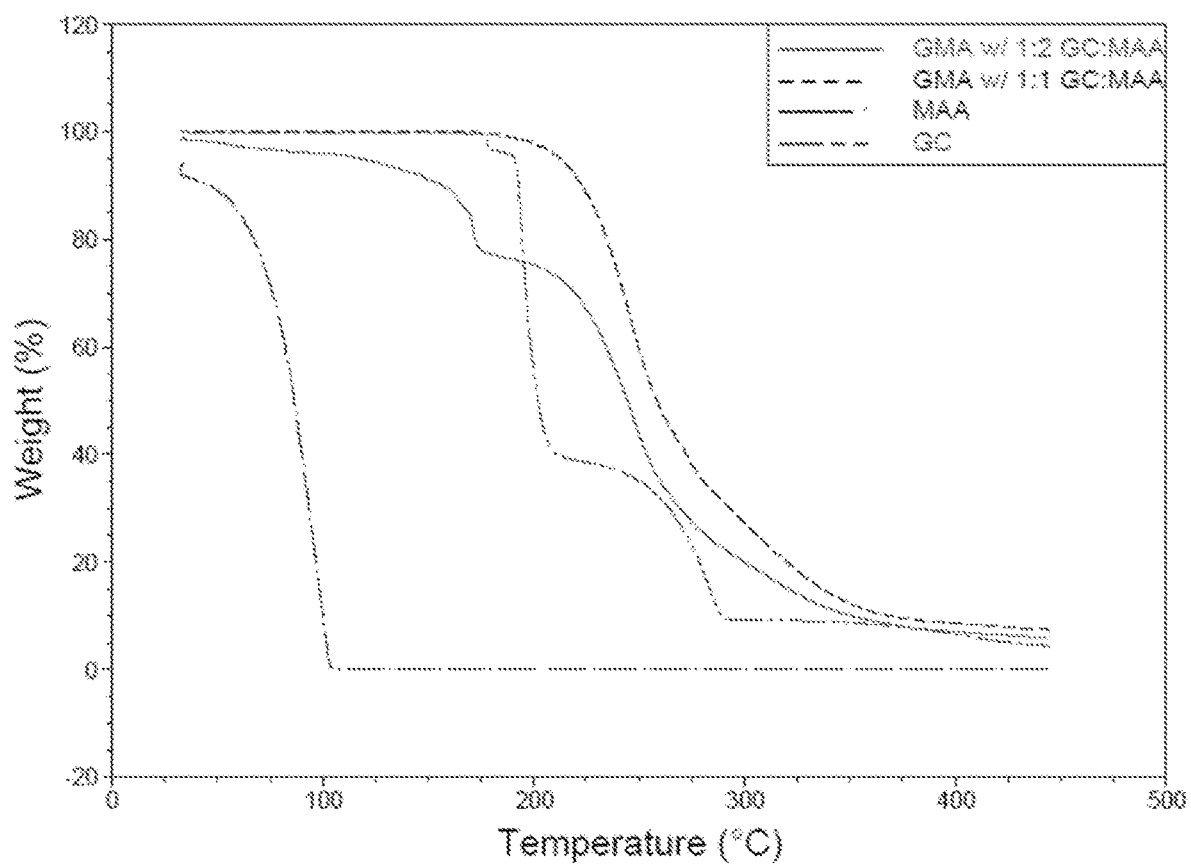
FIG. 1 shows the TGA profile of guanidine methacrylate (GMA) made according to the present disclosure using different molar ratios of guanidine carbonate to methacrylic acid.

As used herein, the terms "a", "an", or "the" means "one or more" or "at least one" and may be used interchangeably, unless otherwise stated.

As used herein, the term "comprises" includes "consists essentially of" and "consists of." The term "comprising" includes "consisting essentially of" and "consisting of."

The first aspect of the present disclosure relates to a process for producing a compound comprising an ethylenically unsaturated organic anion and an organic cation containing a C=N imine group, the process comprising reacting an ethylenically unsaturated organic acid, or anhydride thereof, with an organic base containing a C=N imine group.

The reaction between the ethylenically unsaturated organic acid, or anhydride thereof, with the organic base containing a C=N imine group is generally conducted by mixing the ethylenically unsaturated organic acid, or anhydride thereof, and the organic base containing a C=N imine group in liquid medium, typically aqueous medium. For instance, in one suitable method, the ethylenically unsaturated organic acid is dissolved in the liquid medium and then the organic base containing a C=N imine group is slowly added to the reaction mixture while stirring.

The molar ratio of organic base containing a C=N imine group to ethylenically unsaturated organic acid is typically greater than 0.5. In an embodiment, the molar ratio of organic base containing a C=N imine group to ethylenically unsaturated organic acid is greater than or equal to 1. In another embodiment, the molar ratio of organic base containing a C=N imine group to ethylenically unsaturated organic acid is greater than or equal to 2.

Suitable ethylenically unsaturated organic acids include, but are not limited to, methacrylic acid, acrylic acid, crotonic acid, itaconic acid, citraconic acid, mesaconic acid, maleic acid, fumaric acid, aconitic acid, vinyl sulfonic acid, p-styrene sulfonic acid, methallyl sulfonic acid, 2-acrylamido-2-methyl propane sulfonic acid, and the like.

In another embodiment, the ethylenically unsaturated organic acid is methacrylic acid, acrylic acid, itaconic acid, or a mixture thereof.

As used herein, anhydrides refer to compounds that comprise one or more —(C=O)—O—(C=O)— groups. Such groups are formed by a reaction between two carboxylic acid groups with the release of a water molecule. The two carboxylic acid groups may be on the same molecule or on different molecules. Anhydrides suitable for producing the compound comprising an ethylenically unsaturated organic anion and an organic cation containing a C=N imine group include, but are not limited to, the anhydrides of methacrylic acid, acrylic acid, crotonic acid, itaconic acid, citraconic acid, mesaconic acid, maleic acid, fumaric acid, aconitic acid, vinyl sulfonic acid, p-styrene sulfonic acid, methallyl sulfonic acid, 2-acrylamido-2-methyl propane sulfonic acid, and the like.

The organic base containing a C=N imine group used in the process may be provided in the form of a free base or in the form of a salt. In the case in which the organic base is provided in the form of a salt, the organic base is formed in situ when the salt is at least partially dissolved in a liquid medium, typically aqueous medium. Suitable organic bases containing a C=N imine group include, but are not limited to, guanidine, acetamidine, amidine, six-membered heterocycles, such as pyrimidine, pyrazine, pyridazine, triazine, and derivatives and isomers thereof; five-membered heterocycles, such as imidazole, 4,5-dihydro-1H-imidazole, pyrazole, 1,2,3-triazole, 1,2,4-triazole, tetrazole, and derivatives and isomers thereof; fused ring systems, such as benzimidazole, indazole, benzotriazole, imidazo-pyridine, quinoline, quinozoline, pteridine, and derivatives and isomers thereof.

In an embodiment, the organic base containing a C=N imine group is guanidine, acetamidine, amidine, or pyrimidine; typically guanidine.

As would be apparent to the ordinarily-skilled artisan, the organic cation containing a C=N imine group is derived from the organic base used in the reaction.

In an embodiment, the organic cation containing a C=N imine group is guanidinium ion or acetamidinium ion, amidinium ion, or pyrimidinium ion; typically guanidinium ion.

The compound comprising an ethylenically unsaturated organic anion and an organic cation containing a C=N imine group that is formed may be used as-is, i.e., dissolved in solution, or isolated by methods known to those of ordinary skill in the art, such as removal of solvent by rotoevaporation or distillation with or without filtration followed by drying.

The second aspect of the present disclosure relates to a polymer comprising repeating units derived from a first monomer and repeating units derived from a second monomer different from the first monomer, wherein the second monomer is a compound comprising an ethylenically unsaturated organic anion and an organic cation containing a C=N imine group.

The polymer is typically a polyacrylonitrile-based (PAN) polymer. Thus, in an embodiment, the repeating units derived from the first monomer are repeating units derived from acrylonitrile.

The repeating units derived from the second monomer are repeating units derived from a compound comprising an ethylenically unsaturated organic anion and an organic cation containing a C=N imine group, typically produced according to the process described herein.

The polymer may further comprise repeating units derived from other comonomers. Such repeating units may be derived from suitable comonomers including, but not limited to, vinyl-based acids, such as methacrylic acid (MAA), acrylic acid (AA), and itaconic acid (ITA); vinyl-based esters, such as methacrylate (MA), ethyl acrylate (EA), butyl acrylate (BA), methyl methacrylate (MMA), ethyl methacrylate (EMA), propyl methacrylate, butyl methacrylate, β-hydroxyethyl methacrylate, dimethylaminoethyl methacrylate, 2-ethylhexylacrylate, isopropyl acetate, vinyl acetate (VA), and vinyl propionate; vinyl amides, such as vinyl imidazole (VIM), acrylamide (AAm), and diacetone acrylamide (DAAm); vinyl halides, such as allyl chloride, vinyl bromide, vinyl chloride and vinylidene chloride; ammonium salts of vinyl compounds and sodium salts of sulfonic acids, such as sodium vinyl sulfonate, sodium p-styrene sulfonate (SSS), sodium methallyl sulfonate (SMS), and sodium-2-acrylamido-2-methyl propane sulfonate (SAMPS), among others.

The third aspect of the present disclosure relates to a process for producing the polymer described herein, the process comprising copolymerizing a first monomer, typically acrylonitrile, and a second monomer different from the first monomer, wherein the second monomer is a compound comprising an ethylenically unsaturated organic anion and an organic cation containing a C=N imine group.

The polymer can be made by any polymerization method known to those of ordinary skill in the art. Exemplary methods include, but are not limited to, solution polymerization, dispersion polymerization, precipitation polymerization, suspension polymerization, emulsion polymerization, and variations thereof.

One suitable method comprises mixing the first monomer, typically acrylonitrile (AN) monomer, and the second monomer, which is a compound comprising an ethylenically unsaturated organic anion and an organic cation containing a C=N imine group described herein, in a solvent in which the polymer is soluble, thereby forming a solution. The solution is heated to a temperature above room temperature (i.e., greater than 25° C.), for example, to a temperature of about 40° C. to about 85° C. After heating, an initiator is added to the solution to initiate the polymerization reaction. Once polymerization is completed, unreacted AN monomers are stripped off (e.g., by de-aeration under high vacuum) and the resulting PAN polymer solution is cooled down. At this stage, the polymer is in a solution, or dope, form.

Examples of suitable solvents include, but are not limited to, dimethyl sulfoxide (DMSO), dimethyl formamide (DMF), dimethyl acetamide (DMAc), ethylene carbonate (EC), zinc chloride ($ZnCl_2$)/water and sodium thiocyanate (NaSCN)/water.

In another suitable method, the first monomer, typically acrylonitrile (AN) monomer, and the second monomer, which is the compound comprising an ethylenically unsaturated organic anion and an organic cation containing a C=N imine group, may be polymerized in a medium, typically aqueous medium, in which the resulting polymer is sparingly soluble or non-soluble. In this manner, the resulting polymer would form a heterogenous mixture with the medium. The polymer is then filtered and dried.

The polymerization may employ other comonomers. Examples of suitable comonomers include, but are not limited to, vinyl-based acids, such as methacrylic acid (MAA), acrylic acid (AA), and itaconic acid (ITA); vinyl-based esters, such as methacrylate (MA), ethyl acrylate (EA), butyl acrylate (BA), methyl methacrylate (MMA), ethyl methacrylate (EMA), propyl methacrylate, butyl methacrylate, ß-hydroxyethyl methacrylate, dimethylaminoethyl methacrylate, 2-ethylhexylacrylate, isopropyl acetate, vinyl acetate (VA), and vinyl propionate; vinyl amides, such as vinyl imidazole (VIM), acrylamide (AAm), and diacetone acrylamide (DAAm); vinyl halides, such as allyl chloride, vinyl bromide, vinyl chloride and vinylidene chloride; ammonium salts of vinyl compounds and sodium salts of sulfonic acids, such as sodium vinyl sulfonate, sodium p-styrene sulfonate (SSS), sodium methallyl sulfonate (SMS), and sodium-2-acrylamido-2-methyl propane sulfonate (SAMPS), among others.

The comonomer percentage (amount of one or more comonomers to amount of acrylonitrile) is not particularly limited. However, a suitable comonomer percentage is 0 to 20%, typically 1 to 5%, more typically 1 to 3%.

Suitable initiators (or catalysts) for the polymerization include, but are not limited to, azo-based compounds, such as azo-bisisobutyronitrile (AIBN), 2,2'-azobis[2-(2-imidazolin-2-yl)propane]dihydrochloride, 2,2'-azobis(2-methylpropionamidine)dihydrochloride, 2,2'-azobis[N-(2-carboxyethyl)-2-methylpropionamidine]tetrahydrate, 2,2'-azobis[2-(2-imidazolin-2-yl)propane], 2,2'-azobis[2-methyl-N-(2-hydroxyethyl)propionamide], 4,4'-azobis(4-cyanovaleric acid), 2,2'-azobis-(2,4-dimethyl) valeronitrile (ABVN), among others; and organic peroxides, such as dilauroyl peroxide (LPO), di-tert-butyl peroxide (TBPO), diisopropyl peroxydicarbonate (IPP), among others.

In an embodiment, the copolymerization is conducted with 2,2'-azobis[2-(2-imidazolin-2-yl)propane]dihydrochloride as initiator.

The fourth aspect of the present disclosure relates to a process for producing carbon fibers, the process comprising:
  a) preparing a polymer solution or a molten polymer;
  b) spinning the polymer solution or the molten polymer prepared in step (a); thereby forming carbon fiber precursor fibers;
  c) drawing the carbon fiber precursor fibers through one or more draw and wash baths, resulting in drawn carbon fiber precursor fibers that are substantially free of solvent; and
  d) oxidizing the drawn carbon fiber precursor fibers of step c) to form stabilized carbon fiber precursor fibers and then carbonizing the stabilized carbon fiber precursor fiber, thereby producing carbon fibers;
    wherein the polymer solution or molten polymer comprises the polymer described herein or the polymer made according to the process described herein.

In an embodiment, step (a) comprises preparing a polymer solution.

Preparing the polymer solution may be achieved according to any method known to those of ordinary skill in the art. One suitable method is a method described herein in which the polymer is formed in a medium, typically one or more solvents, such as those already described, in which the polymer is soluble to form a solution.

Another suitable method is a method described herein in which the polymer is formed in a medium, typically aqueous medium, in which the polymer is sparingly soluble or non-soluble to form a mixture, isolating the resulting polymer, for example, by filtration, and dissolving the resulting polymer in one or more solvents, such as those already described, to form a polymer solution.

In another embodiment, step (a) comprises preparing a molten polymer. Preparing the molten polymer may be achieved according to any method known to those having ordinary skill in the art. In a suitable method, preparing the molten polymer comprises forming the polymer in a medium, typically aqueous medium, in which the polymer is sparingly soluble or non-soluble to form a mixture and isolating the resulting polymer, for example, by filtration and then drying. The polymer is then heated until it is in a molten state suitable for processing through a spinneret.

After the polymer solution or molten polymer is prepared, carbon fiber precursor fibers are formed by spinning the polymer solution or molten polymer.

In an embodiment, step (b) comprises spinning the polymer solution prepared in step a) in a coagulation bath. The term "precursor fiber" refers to a fiber comprising a polymeric material that can, upon the application of sufficient heat, be converted into a carbon fiber having a carbon content that is about 90% or greater, and in particular about 95% or greater, by weight.

To make the carbon fiber precursor fibers, the polymer solution (i.e., spin "dope") is subjected to conventional wet spinning and/or air-gap spinning after removing air bubbles by vacuum. The spin dope can have a polymer concentration of at least 10 wt %, typically from about 16 wt % to about 28 wt % by weight, more typically from about 19 wt % to about 24 wt %, based on total weight of the solution. In wet spinning, the dope is filtered and extruded through holes of a spinneret (typically made of metal) into a liquid coagulation bath for the polymer to form filaments. The spinneret holes determine the desired filament count of the fiber (e.g., 3,000 holes for 3K carbon fiber). In air-gap spinning, a vertical air gap of 1 to 50 mm, typically 2 to 10 mm, is provided between the spinneret and the coagulating bath. In this spinning method, the polymer solution is filtered and extruded in the air from the spinneret and then extruded filaments are coagulated in a coagulating bath.

The coagulation liquid used in the process is a mixture of solvent and non-solvent. Water or alcohol is typically used as the non-solvent. Suitable solvents include the solvents described herein. In an embodiment, dimethyl sulfoxide, dimethyl formamide, dimethyl acetamide, or mixtures thereof, is used as solvent. In another embodiment, dimethyl sulfoxide is used as solvent. The ratio of solvent and non-solvent, and bath temperature are not particularly limited and may be adjusted according to known methods to achieve the desired solidification rate of the extruded nascent filaments in coagulation. However, the coagulation bath typically comprises 40 wt % to 85 wt % of one or more solvents, the balance being non-solvent, such as water or alcohol. In an embodiment, the coagulation bath comprises 40 wt % to 70 wt % of one or more solvents, the balance being non-solvent. In another embodiment, the coagulation bath comprises 50 wt % to 85 wt % of one or more solvents, the balance being non-solvent.

Typically, the temperature of the the coagulation bath is from 0° C. to 80° C. In an embodiment, the temperature of the coagulation bath is from 30° C. to 80° C. In another embodiment, the temperature of the coagulation bath is from 0° C. to 20° C.

In another embodiment, step (b) comprises processing the molten polymer prepared in step (a) through a spinneret to form carbon fiber precursor fibers. In this manner, the molten polymer is pumped through a spinneret suitably selected by the ordinarily-skilled artisan for desired properties, such as desired filament count of the fiber. Upon leaving the spinneret, the molten polymer is cooled to form the carbon fiber precursor fibers.

The drawing of the carbon fiber precursor fibers is conducted by conveying the spun precursor fibers through one or more draw and wash baths, for example, by rollers. The carbon fiber precursor fibers are conveyed through one or more wash baths to remove any excess solvent and stretched in hot (e.g., 40° C. to 100° C.) water baths to impart molecular orientation to the filaments as the first step of controlling fiber diameter. The result is drawn carbon fiber precursor fibers that are substantially free of solvent.

In an embodiment, the carbon fiber precursor fibers are stretched from −5% to 30%, typically from 1% to 10, more typically from 3 to 8%.

Step c) of the process may further comprise drying the drawn carbon fiber precursor fibers that are substantially free of solvent, for example, on drying rolls. The drying rolls can be composed of a plurality of rotatable rolls arranged in series and in serpentine configuration over which the filaments pass sequentially from roll to roll and under sufficient tension to provide filaments stretch or relaxation on the rolls. At least some of the rolls are heated by pressurized steam, which is circulated internally or through the rolls, or electrical heating elements inside of the rolls. Finishing oil can be applied onto the stretched fibers prior to drying in order to prevent the filaments from sticking to each other in downstream processes.

In step d) of the process described herein, the drawn carbon fiber precursor fibers of step c) are oxidized to form stabilized carbon fiber precursor fibers and, subsequently, the stabilized carbon fiber precursor fiber are carbonized to produce carbon fibers.

During the oxidation stage, the drawn carbon fiber precursor fibers, typically PAN fibers, are fed under tension through one or more specialized ovens, each having a temperature from 150 to 300° C., typically from 200 to 280° C., more typically from 220 to 270° C. Heated air is fed into each of the ovens. Thus, in an embodiment, the oxidizing in step d) is conducted in an air environment. The drawn carbon fiber precursor fibers are conveyed through the one or more ovens at a speed of from 4 to 100 fpm, typically from 30 to 75 fpm, more typically from 50 to 70 fpm.

The oxidation process combines oxygen molecules from the air with the fiber and causes the polymer chains to start crosslinking, thereby increasing the fiber density to 1.3 g/cm$^3$ to 1.4 g/cm$^3$. In the oxidization process, the tension applied to fiber is generally to control the fiber drawn or shrunk at a stretch ratio of 0.8 to 1.35, typically 1.0 to 1.2. When the stretch ratio is 1, there is no stretch. And when the stretch ratio is greater than 1, the applied tension causes the fiber to be stretched. Such oxidized PAN fiber has an infusible ladder aromatic molecular structure and it is ready for carbonization treatment.

Carbonization results in the crystallization of carbon molecules and consequently produces a finished carbon fiber that has more than 90 percent carbon content. Carbonization of the oxidized, or stabilized, carbon fiber precursor fibers occurs in an inert (oxygen-free) atmosphere inside one or more specially designed furnaces. In an embodiment, carbonizing in step d) is conducted in a nitrogen environment. The oxidized carbon fiber precursor fibers are passed through one or more ovens each heated to a temperature of from 300° C. to 1650° C., typically from 1100° C. to 1450° C.

In an embodiment, the oxidized fiber is passed through a pre-carbonization furnace that subjects the fiber to a heating temperature of from about 300° C. to about 900° C., typically about 350° C. to about 750° C., while being exposed to an inert gas (e.g., nitrogen), followed by carbonization by passing the fiber through a furnace heated to a higher temperature of from about 700° C. to about 1650° C., typically about 800° C. to about 1450° C., while being exposed to an inert gas. Fiber tensioning may be added throughout the precarbonization and carbonization processes. In pre-carbonization, the applied fiber tension is sufficient to control the stretch ratio to be within the range of 0.9 to 1.2, typically 1.0 to 1.15. In carbonization, the tension used is sufficient to provide a stretch ratio of 0.9 to 1.05.

Adhesion between the matrix resin and carbon fiber is an important criterion in a carbon fiber-reinforced polymer composite. As such, during the manufacture of carbon fiber, surface treatment may be performed after oxidation and carbonization to enhance this adhesion.

Surface treatment may include pulling the carbonized fiber through an electrolytic bath containing an electrolyte, such as ammonium bicarbonate or sodium hypochlorite. The chemicals of the electrolytic bath etch or roughen the surface of the fiber, thereby increasing the surface area available for interfacial fiber/matrix bonding and adding reactive chemical groups.

Next, the carbon fiber may be subjected to sizing, where a size coating, e.g. epoxy-based coating, is applied onto the fiber. Sizing may be carried out by passing the fiber through a size bath containing a liquid coating material. Sizing protects the carbon fiber during handling and processing into intermediate forms, such as dry fabric and prepreg. Sizing also holds filaments together in individual tows to reduce fuzz, improve processability and increase interfacial shear strength between the fiber and the matrix resin.

Following sizing, the coated carbon fiber is dried and then wound onto a bobbin.

A person of ordinary skill in the art would understand that the processing conditions (including composition of the spin solution and coagulation bath, the amount of total baths, stretches, temperatures, and filament speeds) are correlated to provide filaments of a desired structure and denier. The process of the present disclosure may be conducted continuously.

In the fifth aspect, the present disclosure relates to carbon fibers produced according to the process described herein.

Carbon fibers produced according to the process described herein may be characterized by mechanical properties, such as tensile strength and tensile modulus per the ASTM D4018 test method.

The processes and carbon fibers produced therefrom of the present disclosure are further illustrated by the following non-limiting examples.

EXAMPLES

Example 1. Synthesis of Guanidine Methacrylate Monomer

Guanidine methacrylate (GMA) was synthesized as follows. Methacrylic acid (MAA) was dissolved in distilled water in a reaction flask. Guanidine carbonate (GC) was slowly added to the reaction solution while stirring. Evolution of carbon dioxide gas was observed and the process continued until the carbon dioxide gas was eliminated.

The synthesis of GMA was conducted with a molar ratio of guanidine carbonate to methacrylic acid of 1:2 (or 0.5) and a molar ratio of 1:1 (or 1).

The GMA product from each experiment was analyzed by thermal gravimetric analysis (TGA). TGA was carried out on a TA Instruments DSC Q600, with Universal Analysis 2000. FIG. 1 shows the TGA profile of GMA made using a molar ratio of guanidine carbonate to methacrylic acid of 1:2 (or 0.5) and the TGA profile of GMA made using a molar ratio of 1:1 (or 1). As shown in FIG. 1, better conversions were observed when the molar ratio of GC to MAA was 1:1 instead of 1:2.

Example 2. Synthesis of Guanidine Itaconate Monomer

Guanidine itaconate (GIA) was synthesized as follows. Itaconic acid (ITA) was dissolved in distilled water in a reaction flask. Guanidine carbonate (GC) was slowly added to the reaction solution while stirring. Evolution of carbon dioxide gas was observed and the process continued until the carbon dioxide gas was eliminated. The reaction solvent was removed by rotoevaporation or distillation.

The synthesis of GIA was conducted with a molar ratio of guanidine carbonate to itaconic acid of 1:1 (or 1) and a molar ratio of 2:1 (or 2).

Figure 2:
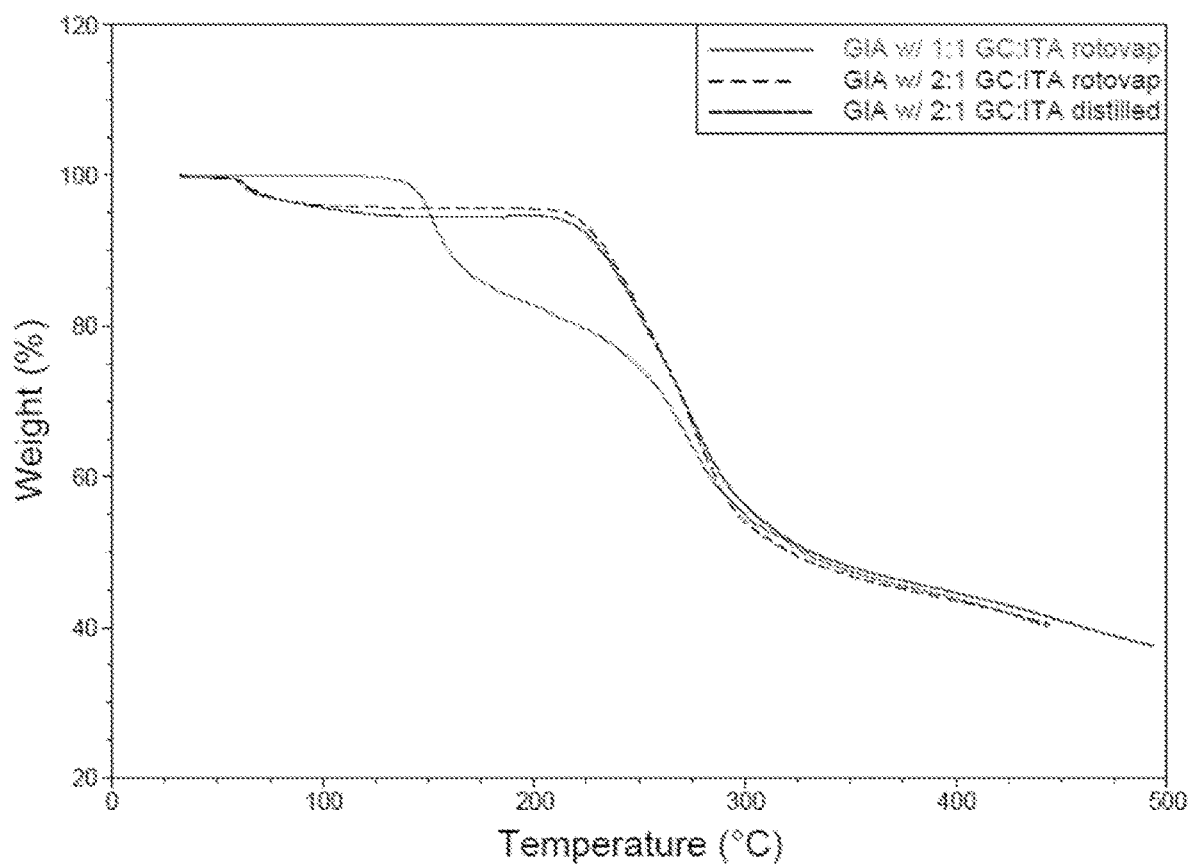
FIG. 2 shows the TGA profile of guanidine itaconate (GIA) made according to the present disclosure using different molar ratios of guanidine carbonate to itaconic acid.

The GIA product from each experiment was analyzed by thermal gravimetric analysis (TGA) as in Example 1. FIG. 2 shows the TGA profile of GIA made using a molar ratio of guanidine carbonate to itaconic acid of 1:1 (or 1) and the TGA profile of GIA made using a molar ratio of guanidine carbonate to itaconic acid of 2:1 (or 2). As shown in FIG. 2, better conversions were observed when the molar ratio of GC to ITA was 2:1 instead of 1:1. The effect of solvent removal by rotoevaporation or distillation was minimal.

What is claimed is:

1. A process for producing carbon fibers, the process comprising:
   a) preparing a polymer solution or a molten polymer;
   b) spinning the polymer solution or the molten polymer prepared in step (a); thereby forming carbon fiber precursor fibers;
   c) drawing the carbon fiber precursor fibers through one or more draw and wash baths, resulting in drawn carbon fiber precursor fibers that are substantially free of solvent; and
   d) oxidizing the drawn carbon fiber precursor fibers of step c) to form stabilized carbon fiber precursor fibers and then carbonizing the stabilized carbon fiber precursor fiber, thereby producing carbon fibers;
   wherein the polymer solution or molten polymer comprises a polymer comprising repeating units derived from a first monomer and repeating units derived from a second monomer different from the first monomer, wherein the second monomer is a compound comprising an ethylenically unsaturated organic anion and an organic cation containing a C=N imine group produced by reacting an ethylenically unsaturated organic acid, or anhydride thereof, with an organic base containing a C=N imine group.

2. The process according to claim 1, wherein the organic cation containing a C=N imine group is guanidinium ion or acetamidinium ion, amidinium ion, or pyrimidinium ion.

3. The process according to claim 1, wherein the organic base containing a C=N imine group is guanidine, acetamidine, amidine, or pyrimidine.

4. The process according to claim 1, wherein the ethylenically unsaturated organic acid, or anhydride thereof, is selected from the group consisting of methacrylic acid, acrylic acid, crotonic acid, itaconic acid, citraconic acid, mesaconic acid, maleic acid, fumaric acid, aconitic acid, vinyl sulfonic acid, p-styrene sulfonic acid, methallyl sulfonic acid, and 2-acrylamido-2-methyl propane sulfonic acid, anhydrides thereof, and mixtures thereof.

5. The process according to claim 1, wherein the ethylenically unsaturated organic acid is methacrylic acid, acrylic acid, itaconic acid, or a mixture thereof.

6. The process according to claim 1, wherein step (b) comprises spinning the polymer solution prepared in step (a) in a coagulation bath.

7. The process according to claim 1, wherein step (b) comprises processing the molten polymer prepared in step (a) through a spinneret.

8. Carbon fibers produced according to claim 1.

9. The process according to claim 1, wherein the organic cation containing a C=N imine group is guanidinium ion.

10. The process according to claim 1, wherein the organic base containing a C=N imine group is guanidine.

11. The process according to claim 1, wherein the first monomer is acrylonitrile.

12. A process for producing carbon fibers, the process comprising:

a) preparing a polymer solution or a molten polymer;
b) spinning the polymer solution or the molten polymer prepared in step (a); thereby forming carbon fiber precursor fibers;
c) drawing the carbon fiber precursor fibers through one or more draw and wash baths, resulting in drawn carbon fiber precursor fibers that are substantially free of solvent; and
d) oxidizing the drawn carbon fiber precursor fibers of step c) to form stabilized carbon fiber precursor fibers and then carbonizing the stabilized carbon fiber precursor fiber, thereby producing carbon fibers;
wherein the polymer solution or molten polymer comprises a polymer comprising repeating units derived from a first monomer and repeating units derived from a second monomer different from the first monomer, wherein the second monomer is a compound comprising an ethylenically unsaturated organic anion and an organic cation containing a C=N imine group, the polymer being made by process comprising copolymerizing a first monomer and a second monomer different from the first monomer, wherein the second monomer is a compound comprising an ethylenically unsaturated organic anion and an organic cation containing a C=N imine group produced by reacting an ethylenically unsaturated organic acid, or anhydride thereof, with an organic base containing a C=N imine group.

13. The process according to claim 12, wherein the comonomer percentage is 0 to 20%.

14. The process according to claim 12, wherein the copolymerization is conducted with 2,2'-azobis[2-(2-imidazolin-2-yl)propane]dihydrochloride as initiator.

15. The process according to claim 12, wherein the first monomer is acrylonitrile.

16. The process according to claim 13, wherein the comonomer percentage is 1 to 5%.

17. The process according to claim 16, wherein the comonomer percentage is 1 to 3%.

* * * * *